United States Patent
Harlev

(10) Patent No.: US 10,550,025 B2
(45) Date of Patent: Feb. 4, 2020

(54) COMPOSITIONS AND METHODS FOR REMOVAL OF CYCLIC AND LINEAR ORGANIC COMPOUNDS

(71) Applicant: Ilana Harlev, Rehovot (IL)

(72) Inventor: Ilana Harlev, Rehovot (IL)

(*) Notice: Subject to any disclaimer, the term of this patent is extended or adjusted under 35 U.S.C. 154(b) by 0 days.

(21) Appl. No.: 15/750,206

(22) PCT Filed: Aug. 3, 2016

(86) PCT No.: PCT/IL2016/050849
§ 371 (c)(1),
(2) Date: Feb. 5, 2018

(87) PCT Pub. No.: WO2017/021966
PCT Pub. Date: Feb. 9, 2017

(65) Prior Publication Data
US 2018/0257963 A1    Sep. 13, 2018

Related U.S. Application Data

(60) Provisional application No. 62/201,122, filed on Aug. 5, 2015.

(51) Int. Cl.
| | |
|---|---|
| *C02F 3/34* | (2006.01) |
| *C02F 1/68* | (2006.01) |
| *C02F 101/16* | (2006.01) |
| *C02F 101/34* | (2006.01) |
| *C02F 101/38* | (2006.01) |
| *C02F 103/42* | (2006.01) |

(52) U.S. Cl.
CPC .............. *C02F 3/342* (2013.01); *C02F 1/688* (2013.01); *C02F 2101/16* (2013.01); *C02F 2101/34* (2013.01); *C02F 2101/38* (2013.01); *C02F 2103/42* (2013.01); *C02F 2303/04* (2013.01); *C02F 2303/18* (2013.01)

(58) Field of Classification Search
None
See application file for complete search history.

(56) References Cited

U.S. PATENT DOCUMENTS

| | | |
|---|---|---|
| 2010/0270228 A1 | 10/2010 | Teichberg |
| 2011/0127208 A1 | 6/2011 | Sadowsky et al. |
| 2015/0353399 A1 | 12/2015 | Wackett et al. |

OTHER PUBLICATIONS

Yeom et al. Bacterial Cyanuric Acid Hydrolase for Water Treatment, Applied and Environmental Microbiology, 81(19), 6660-6665, 2015, EPub Jul. 10, 2015.*
Janssen et al. Nitrogen Control in Pseudomonas aeruginosa: Mutants Affected in the Synthesis of Glutamine Synthetase, Urease, and NADP-Dependent Glutamate Dehydrogenase. Journal of Bacteriology, Jul. 1982, 151(1): p. 22-28.*
Yeom S. et al, "Bacterial cyanuric acid hydrolase for water treatment." Applied and environmental microbiology, 81(19), 6660-6668. Jul. 17, 2015.
Shapir, N. et al, "Purification and characterization of TrzF:biuret hydrolysis by allophanate hydrolase supports growth." Applied and environmental microbiology, 72(4), 2491-2495. Jun. 30, 2005.
Cameron, S. et al, "New family of biuret hydrolases involved in s-triazine ring metabolism." ACS catalysis, 1(9), 1075-1082. Aug. 1, 2011.
Cheng, G. et al, "Allophanate hydrolase, not urease, functions in bacterial cyanuric acid metabolism." Applied and environmental microbiology, 71(8), 4437-4445. Aug. 31, 2005.
Canelli E.,"Chemical bacteriological, and toxicological properties of cyanuric acid and chlorinated isocyanurates as applied to swimming pool disinfection: a review." American journal of public health, 64(2), 155-162. Feb. 28, 1974.
Dobson, R.L., "Identification and characterization of toxicity of contaminants in pet food leading to an outbreak of renal toxicity in cats and dogs." Toxicological Sciences, 106(1), 251-262. Aug. 9, 2008.

* cited by examiner

*Primary Examiner* — Iqbal H Chowdhury
(74) *Attorney, Agent, or Firm* — JMB Davis Ben-David

(57) ABSTRACT

Described herein are compositions for removing cyanuric acid from an environment, and methods of use thereof for removing cyanuric acid and its metabolite from an environment, such as a body of water.

12 Claims, 7 Drawing Sheets

Specification includes a Sequence Listing.

Figure 4

| Swimming pool no. | CYA (ppm) | | |
|---|---|---|---|
|  | 0 min. | 60 min. | 48 hr. |
| 1 | 57 | <5 | <5 |
| 2 | 64 | <5 | <5 |
| 3 | 60 | <5 | <5 |

| Swimming pool no. | Ammonia (mM) | | |
|---|---|---|---|
|  | 4 hr. | 24 hr. | 48 hr. |
| 1 | 0.316 | 1.076 | 1.093 |
| 2 | 0.162 | 0.985 | 1.065 |
| 3 | 0.280 | 1.373 | 1.199 |

Figure 5A

Cyanuric acid amidohydrolase (*AtzD*) (363 aa protein)

>gi|695226252|ref|YP_009089919.1| cyanuric acid amidohydrolase [Pseudomonas sp. ADP]

MYHIDVFRIPCHSPGDTSGLEDLIETGRVAPADIVAVMGKTEGNGCVNDYTREYATAMLAACLGRHLQLP
PHEVEKRVAFVMSGGTEGVLSPHHTVFARRPAIDAHRPAGKRLTLGIAFTRDFLPEEIGRHAQITETAGA
VKRAMRDAGIASIDDLHFVQVKCPLLTPAKIASARSRGCAPVTTDTYESMGYSRGASALGIALATEEVPS
SMLVDESVLNDWSLSSSLASASAGIELEHNVVIAIGMSEQATSELVIAHGVMSDAIDAASVRRTIESLGI
RSDDEMDRIVNVFAKAEASPDGVVRGMRHTMLSDSDINSTRHARAVTGAAIASVVGHGMVYVSGGAEHQG
PAGGGPFAVIARA

Figure 5B

Biuret amidohydrolase (*AtzE*) (457 aa protein)

>gi|32455885|ref|NP_862538.1| biuret hydrolase [Pseudomonas sp. ADP]

MKTVEIIEGIASGRTSARDVCEEALATIGATDGLINAFTCRTVERARAEADAIDVRRARGEVLPPLAGLP
YAVKNLFDIEGVTTLAGSKINRTLPPARADAVLVQRLKAAGAVLLGGLNMDEFAYGFTTENTHYGPTRNP
HDTGRIAGGSSGGSGAAIAAGQVPLSLGSDTNGSIRVPASLCGVWGLKPTFGRLSRRGTYPFVHSIDHLG
PLADSVEGLALAYDAMQGPDPLDPGCSASRIQPSVPVLSQGIAGLRIGVLGGWFRDNAGPAARAAVDVAA
LTLGASEVVMWPDAEIGRAAAFVITASEGGCLHLDDLRIRPQDFEPLSVDRFISGVLQPVAWYLRAQRFR
RVYRDKVNALFRDWDILIAPATPISAPAIGTEWIEVNGTRHPCRPAMGLLTQPVSFAGCPVVAAPTWPGE
NDGMPIGVQLIAAPWNESLCLRAGKVLQDTGIARLKC

Figure 5C

Allophanate hydrolase (*AtzF*) (605 aa protein)

>gi|32455886|ref|NP_862539.1| allophanate hydrolase [Pseudomonas sp. ADP]

MNDRAPHPERSGRVTPDHLTDLASYQAAYAAGTDAADVISDLYARIKEDGENPIWISLLPLESALAMLAD
AQQRKDKGEALPLFGIPFGVKDNIDVAGLPTTAGCTGFARTPRQHAFVVQRLVDAGAIPIGKTNLDQFAT
GLNGTRTPFGIPRCVFNENYVSGGSSSGSAVAVANGTVPFSLGTDTAGSGRIPAAFNNLVGLKPTKGLFS
GSGLVPAARSLDCISVLAHTVDDALAVARVAAGYDADDAFSRKAGAAALTEKSWPRRFNFGVPAAEHRQF
FGDAEAEALFNKAVRKLEEMGGTCISFDYTPFRQAAELLYAGPWVAERLAAIESLADEHPEVLHPVVRDI
ILSAKRMSAVDTFNGIYRLADLVRAAESTWEKIDVMLLPTAPTIYTVEDMLADPVRLNSNLGFYTNFVNL
MDLSAIAVPAGFRTNGLPFGVTFIGRAFEDGAIASLGKAFVEHDLAKGNAATAAPPKDTVAIAVVGAHLS
DQPLNHQLTESGGKLRATTRTAPGYALYALRDATPAKPGMLRDQNAVGSIEVEIWDLPVAGFGAFVSEIP
APLGIGTITLEDGSHVKGFLCEPHAIETALDITHYGGWRAYLAAQ

Figure 6A

Biuret cysteine hydrolase

MDAMVETNRHFIDADPYPWPYNGALRPDNTALIIIDMQTDFCGKGGYVDHMGYDLSLVQA
PIEPIKRVLAAMRAKGYHIIHTREGHRPDLADLPANKRWRSQRIGAGIGDPGPCGRILTR
GEPGWDIIPELYPIEGETIIDKPGKGSFCATDLELVLNQKRIENIILTGITTDVCVSTTM
REANDRGYECLLLEDCCGATDYGNHLAAIKMVKMQGGVFGSVSNSAALVEALP

Figure 6B

```
  1 atggacgcga tggtcgaaac caaccggcat tttatcgacg ccgatccgta tccgtggccc
 61 tataacggag ctctgaggcc tgacaatacc gccctcatca tcatcgacat gcagacggat
121 ttctgcggca agggcggtta tgtcgaccac atgggctacg acctgtcgct ggtgcaggcg
181 ccgatcgaac ccatcaaacg cgtgcttgcc gccatgcggg ccaagggtta tcacatcatc
241 cacacccgcg agggccaccg ccccgacctc gccgatctgc cagcaaacaa acgctggcgc
301 tcgcaacgga tcgggccggcatcggtgat cccggcccct gcggccgaat cctgacgcgt
361 ggcgaaccgg gctgggacat catccccgaa ctctacccga tcgaaggcga gacgatcatc
421 gacaagcccg gcaagggttc gttctgcgcc accgacctcg aactcgtcct caaccagaaa
481 cgcatcgaga acattatcct caccgggatc accaccgatg tctgcgtctc gacgacgatg
541 cgcgaggcga acgaccgcgg ctacgaatgc ctgctgctgg aggactgctg tggtgcgacc
601 gactacggaa accacctcgc cgccatcaag atggtgaaga tgcagggcgg cgtcttcggc
661 tcggtctcca attccgcggc tctagtcgag gcgctgccct ga
```

Figure 7

*Oleomonas sagaranensis*

Allophanate hydrolase (600 aa protein)

```
>gi|46409053|dbj|BAD16655.1| allophanate hydrolase homologue [Oleomonas
sagaranensis]
```

MTLPKMLTIGTLAAAYEAGTLTPLDVIEGVIERLNAWPDPAVWISRFSDDDLRAAAKALVDAGGPSPDKP
LWGIPFAVKDNIDCAGLDTTAACPAFAYTPTQDATVVARLRAAGAIPVGKTNLDQFATGLNGTRSPYGAP
RSVFNADYISGGSSSGSAVSVGAGIVAFSLGTDTAGSGRVPASFNNLVGVKPSKGMFSNTGLVPACRSLD
CISIFAATAGEADFVRRIAAALDPSDPFSRDLPDVVLPTEGLRVGVPVGAEREFFGDSANEAIYVGAIET
MKALGCSIVEIDFAPFREAANLLYSGPWVAERLAAVEAFHAAHADAMDPNVRTIVEGAFGVTAVDAFRGI
YALEGYRQKTASTWAMVDILLLPTTPLFPKVSEMLADPIGLNSKLGRYTNFVNLMDCAGIAVPAGFRPDG
LPFGVTLIGPAFSDAALAVWGDRLHKASATGFGLDTTADLAAMPAPEGPDVERIEVVVVGAHLSGMPLNP
QLTSGGGVLVKSCRTAPDYRLYALPGTVPPKPGLIHSPGFDGPGLAVEVWALPPAAFGRFVAAIPAPLGI
GKVTLDDGSDVSGFLCEAHALEGAVEITALGGWRAYCAAK

Lanes

|  | M | 1 | 2 | 3 | 4 | 5 | 6 | 7 | 8 |
|---|---|---|---|---|---|---|---|---|---|
| Enz |  | Cyanuric acid amidohydrolase | | Biuret cysteine hydrolase | | Allophanate hydrolase from *Pseudomonas* | | Allophanate hydrolase from *Oleomonas sagaranensis* | |
| Incubation |  | ON | | ON | | ON | | ON | |
| Temp. |  | 25° | 25° | 25° | 25° | 16° | 16° | 16° | 16° |
| Fraction |  | Total | Sup | Total | Sup | Total | Sup | Total | Sup |

COMPOSITIONS AND METHODS FOR REMOVAL OF CYCLIC AND LINEAR ORGANIC COMPOUNDS

CROSS REFERENCE TO RELATED APPLICATIONS

This is the U.S. National Stage of International Patent Application No. PCT/IL2016/050849, filed on Aug. 3, 2016, which was published in English under PCT Article 21(2), which in turn claims the benefit of U.S. Provisional Patent Application No. 62/201,122, filed Aug. 5, 2015; the contents of which are incorporated by reference herein in their entirety.

FIELD

Provided herein are compositions for removing cyanuric acid from an environment, and methods of use thereof for removing cyanuric acid and its metabolite from an environment, such as a body of water.

BACKGROUND

Chlorine as such, or in its various forms, is the main sterilization chemical used to control unwanted bacterial and algal growth in closed or semi-closed water reservoirs. The amount of chlorine required to maintain an effective microbicidal chlorine level in swimming pool water for example, depends in part on the chlorine demand of the water, e.g., from pollution brought in by the bathers. Additional factors that increase the chlorine demand are windblown dust, leaves and grass clippings, and other environmental contaminants.

There are a variety of ways to introduce chlorine into water. The most widely used method is addition of hypochlorites of sodium, calcium or lithium. Each of these salts has advantages and disadvantages in price and solubility. $HOCl^-$ generating chemicals such as di- and tri-chloro cyanuric acid are also used to produce hypochlorite.

Once in the water, equilibrium is established between the strong oxidant $HClO^-$ and the weaker $ClO^-$ ion. The equilibrium is pH dependent and is very sensitive in the range of pH 7 to 8. The negative charge on the hypochlorite ion hinders passage through bacterial membranes, so HOCl– is the preferred species to oxidize the cell contents of the bacteria. HOCl– is about 80 times more effective than the OCl– anion in killing microorganisms. Conversion of almost all free chlorine to $HOCl^-$ is easily accomplished by dropping the pH to about 6.

The use of $HOCl^-$ as the active biocide is limited by its sensitivity to heat and UV radiation of the sun, which results in relatively fast degradation into inactive species at ambient environmental conditions. These degrading conditions are heightened in the summer. The inclusion of cyanuric acid (CYA) in water treatment systems stabilizes and thus slows the degradation process of chlorine by sunlight, but it also shifts the equilibrium reaction to compensate for losses of $OCl^-$. Therefore a continuous drop in the amount of the active form of chlorine occurs, and so additional chlorine salt must be continuously added.

As noted, CYA is beneficial for the protection of chlorine loss by UV radiation (in sunlight) at around 20-30 ppm. However, since most commonly used $HOCl^-$-generating chemicals comprise di- and tri-chloro cyanuric acid, as the season progress, the level of the stabilizer (CYA) keeps rising with each cycle of replenishment of the sanitizer ($HOCl^-$), which is constantly lost.

In certain situations, and as a result of over-stabilization, cyanuric acids are too high, and the chlorine is trapped and thus not effective as a disinfectant. This state, which is known as "chlorine-lock", takes place when the concentration of cyanuric acid, which is rather stable, reaches over 100 ppm (corresponding to 0.77 mM). At this level the water is no longer safe for its original use, due a marked decrease in microbicidal efficacy of chlorine under "chlorine lock" conditions.

For these reasons, care is required to maintain relatively low levels of cyanuric acid in water purification contexts. Presently, this is achieved by the removal of cyanuric acid from the pool water either by dilution with fresh water or by emptying the pool, practices not only environmentally wasteful, but also generally impracticable for water reservoirs. Certain chemical procedures have been proposed for the removal of cyanuric acid but they too are unpractical (see for example, U.S. Pat. No. 4,793,935). Moreover, while CYA degradation can be accomplished enzymatically, the resultant CYA metabolites also build up in the water. Thus, there is a continuing need for methods to maintain low levels of cyanuric acid and its metabolites in water being treated with chlorine stabilizers.

SUMMARY

Described herein are compositions for removing cyanuric acid and metabolites thereof from a liquid, which include at least one microbial cell culture, ground cells, extract thereof, or soluble protein fraction thereof, comprising cyanuric acid amidohydrolase, biuret cysteine hydrolase and allophanate hydrolase, or functional variants thereof.

Additionally described herein are compositions for removing cyanuric acid and metabolites thereof from a liquid, which include isolated cyanuric acid amidohydrolase or a functional variant thereof, isolated biuret cysteine hydrolase or a functional variant thereof and isolated allophanate hydrolase or a functional variant thereof.

Also provided herein are methods of removing cyanuric acid from a liquid by providing an effective amount of any of the described compositions to the liquid, thereby removing cyanuric acid from the liquid.

The foregoing and other objects, features, and advantages will become more apparent from the following detailed description, which proceeds with reference to the accompanying figures.

BRIEF DESCRIPTION OF THE DRAWINGS

FIG. 4 shows the in situ biodegradation of CYA and resultant ammonia release using *Pseudomonas* NRRLB 12228 cell lysate and *Rhizobium leguminosarum* bv. *viciae* strain 3841 cell lysate in swimming pool water. The results of three separate pools at the initial, 1-hour, and 48-hour time points are shown for CYA degradation as well as 4-hour, 24-hour, and 48-hour time points for ammonia liberation.

FIGS. 5A-C show the amino acid sequences of *Pseudomonas* sp. ADP, cyanuric acid amidohydrolase (FIG. 5A), biuret amidohydrolase (FIG. 5B), and allophanate hydrolase (FIG. 5C) (SEQ ID NOs: 1-3, respectively)

FIGS. 6A and B show the amino acid (FIG. 6A) and nucleic acid (FIG. 6B) sequence of *Rhizobium leguminosarum* bv. *viciae* strain 3841 biuret cysteine hydrolase (SEQ ID NOs: 4-5, respectively)

FIG. 7 shows the amino acid sequence of *Oleomonas sagaranensis* allophanate hydrolase (SEQ ID NO: 6).

BRIEF DESCRIPTION OF DESCRIBED SEQUENCES

Figure 1:
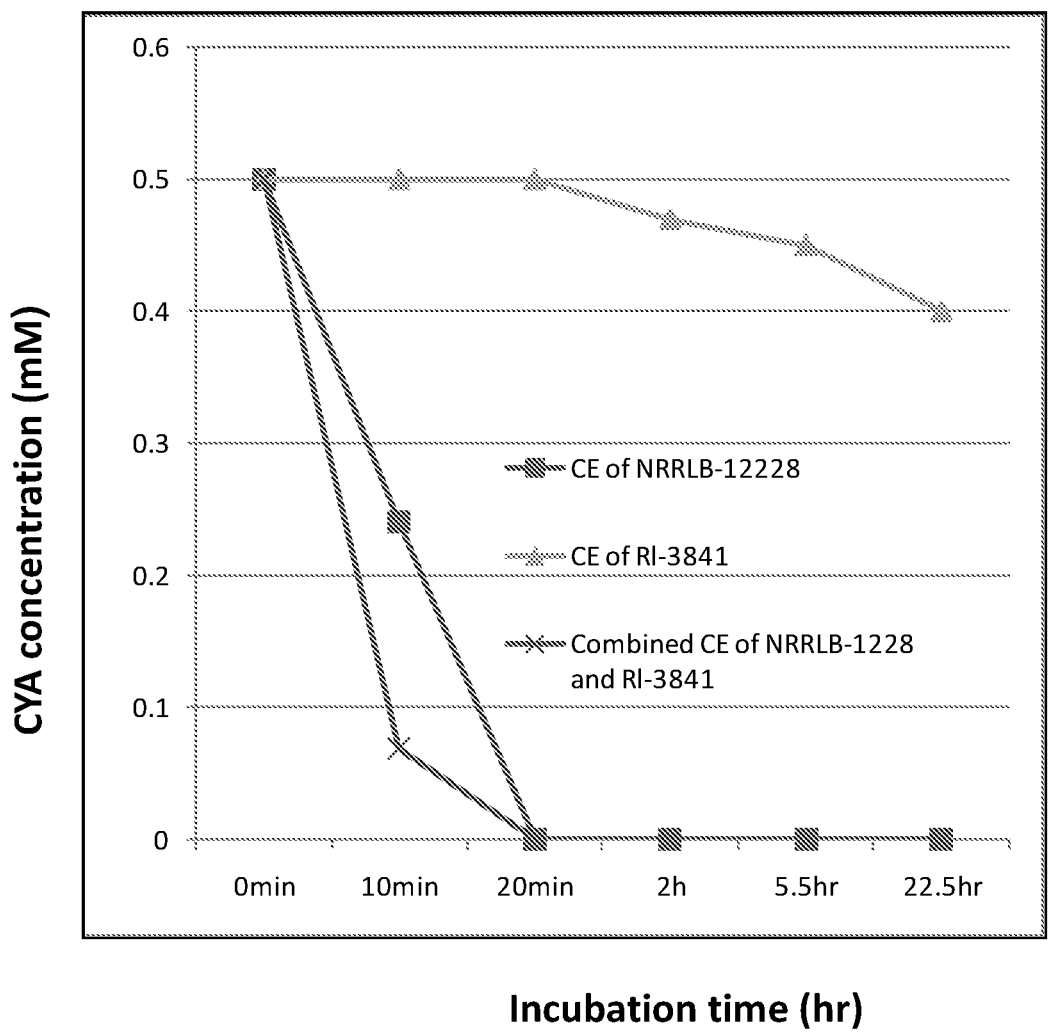
FIG. 1 is a graph showing cyanuric acid (CYA) biodegradation following incubation of 0.5 mM CYA and endogenous enzymes. Crude extracts (diluted 1:200) of *Pseudomonas* NRRLB 12228 cells (squares), *Rhizobium leguminosarum* bv. *viciae* strain 3841 (triangles), or a combination of the two (Xes), were incubated with 0.5 mM CYA in 10 mM sodium phosphate buffer for the indicated time points at 30° C. Cyanuric acid concentrations were measured with C401 kit.

The nucleic and amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 3096 1 2 SeqList.txt, created Aug. 3, 2016, about 20 KB, which is incorporated by reference herein. In the accompanying sequence listing:

SEQ ID NO: 1 is the amino acid sequence of *Pseudomonas* sp. ADP, cyanuric acid amidohydrolase.

SEQ ID NO: 2 is the amino acid sequence of *Pseudomonas* sp. ADP, biuret amidohydrolase.

SEQ ID NO: 3 is the amino acid sequence of *Pseudomonas* sp. ADP, allophanate hydrolase.

SEQ ID NO: 4 is the amino acid sequence of *Rhizobium leguminosarum* bv. *viciae* strain 3841 biuret cysteine hydrolase (a biuret hydrolase of the cysteine hydrolase superfamily).

SEQ ID NO: 5 is the nucleic acid sequence of *Rhizobium leguminosarum* bv. *viciae* strain 3841 biuret cysteine hydrolase (a biuret hydrolase of the cysteine hydrolase superfamily).

SEQ ID NO: 6 is the amino acid sequence of *Oleomonas sagaranensis* allophanate hydrolase.

DETAILED DESCRIPTION

I. Abbreviations

CYA Cyanuric acid
PPM Parts per million
AtzD *Pseudomonas* sp. ADP, cyanuric acid amidohydrolase.
AtzE *Pseudomonas* sp. ADP, biuret amidohydrolase.
AtzF *Pseudomonas* sp. ADP, allophanate hydrolase.

II. Terms

Unless otherwise noted, technical terms are used according to conventional usage. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Allophanate hydrolase: An enzyme that catalyzes the hydrolysis of allophanate to $HCO_3^-$ and $NH_4^+$. Non-limiting examples of allophanate hydrolase include allophanate hydrolase (AtzF) from *Pseudomonas* sp. ADP and allophanate hydrolase from *Oleomonas sagaranensis*. Allophanate hydrolase activity has also been classified by the enzyme classification number EC 3.5.1.54.

Biuret amidohydrolase: An enzyme that catalyzes the hydrolysis of biuret to allophanate and $NH_3$. A non-limiting example includes biuret amidohydrolase (AtzE) from *Pseudomonas* sp. ADP. Biuret amidohydrolase activity has also been classified by the enzyme classification number EC 3.5.1.84.

Biuret cysteine hydrolase: An enzyme that catalyzes the hydrolysis of biuret to allophanate and $NH_3$, but in contrast to biuret amidohydrolase, biuret cysteine hydrolase as used herein refers to a biuret hydrolase of the cysteine hydrolase super family enzymes discovered in *Rhizobium* (Cameron et al., *ACS Catal.* 2011, 1075-1082).

Contacting: Placement in direct physical association. Includes both in solid and liquid form.

Cell culture extract: Interchangeably used herein with "soluble crude extract," "cell extract," or "extract." Refers to a fraction of a bacterium derived from the cytosol. For example, the soluble crude extract may be obtained by lysis of bacteria by any means known in the art, centrifugation of the lysed bacteria and collection of the supernatant. In certain embodiments, the soluble crude extract is in the form of a powder, such as a lyophilized powder. It should be understood that the soluble crude extract is substantially void of intact cells and that the enzymes present in the soluble crude extract are not substantially enclosed in a cell, either dead, alive or cross-linked. This applies also to the protein precipitate of the crude extract.

Cyanuric acid (CYA): The common name for 1,3,5-triazine-2,4,6-triol; a molecule having a chemical formula of $(CNOH)_3$. CYA is commonly used as part of water disinfectant systems, either as a precursor to and/or stabilizer of microbicidal chlorine ions. CYA at lower concentrations (around 30 ppm) acts as an effective stabilizer; but at higher concentrations, CYA will trap chlorine, greatly reducing its efficacy as a water disinfectant.

Cyanuric acid amidohydrolase: An enzyme that catalyzes the hydrolysis of cyanuric acid to biuret and $CO_2$. A non-limiting example includes cyanuric acid amidohydrolase (AtzD) from *Pseudomonas* sp. ADP. Cyanuric acid amidohydrolase activity has also been classified by the enzyme classification number EC 3.5.2.15.

Effective amount of a compound: A quantity of compound sufficient to achieve a desired effect in an environment, such as a body of water. An effective amount of a compound can be administered in a single dose, or in several doses. However, the effective amount of the compound will be dependent on the compound applied and the desired effect.

Encode: A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. A polynucleotide can be inserted into an expression vector (also described herein as a "recombinant plasmid") that contains a promoter sequence, and which facilitates the efficient transcription of the inserted genetic sequence of the host. The expression vector typically contains an origin of replication, a promoter, as well as specific nucleic acid sequences that allow phenotypic selection of the transformed cells.

Functional fragments and variants of a polypeptide: Included are those fragments and variants that maintain one or more functions of the parent polypeptide. It is recognized that the gene or cDNA encoding a polypeptide can be considerably mutated without materially altering one or more the polypeptide's functions. First, the genetic code is well-known to be degenerate, and thus different codons encode the same amino acids. Second, even where an amino acid substitution is introduced, the mutation can be conservative and have no material impact on the essential functions of a protein. Third, part of a polypeptide chain can be deleted without impairing or eliminating all of its functions. Fourth, insertions or additions can be made in the polypeptide chain for example, adding epitope tags, without impairing or eliminating its functions. Other modifications that can be made without materially impairing one or more functions of a polypeptide include, for example, in vivo or in vitro chemical and biochemical modifications or the incorporation of unusual amino acids. Functional fragments and variants can be of varying length. For example, some fragments have at least 10, 25, 50, 75, 100, or 200 amino acid residues.

Gene expression: The process by which the coded information of a nucleic acid transcriptional unit (including, for example, genomic DNA or cDNA) is converted into an operational, non-operational, or structural part of a cell, often including the synthesis of a protein. Gene expression, which is also termed herein as "expression" can occur "genomically," that is, from a genomic source. Expression can also occur from a recombinant plasmid or expression vector.

Isolated: A biological component (such as a nucleic acid molecule, protein or organelle) that has been substantially separated or purified away from other biological components in the cell of the organism in which the component naturally occurs, i.e., other chromosomal and extra-chromosomal DNA and RNA, proteins and organelles. Nucleic acids and proteins that have been isolated include nucleic acids and proteins purified by standard purification methods. The term also embraces nucleic acids and proteins prepared by recombinant expression in a host cell as well as chemically synthesized nucleic acids.

Microbial cell culture: A culture of a microbial cell, whether in solid or liquid form. Thus, in particular embodiments, a microbial cell culture can be a liquid culture, a colony or derived from a colony, or a dried version of a liquid or solid culture.

Operably linked sequence: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Purified: The term purified does not require absolute purity; rather, it is intended as a relative term. Thus, for example, a purified protein preparation is one in which the protein referred to is more pure than the protein in its natural environment within a cell.

Recombinant: A nucleic acid that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

Vector: A nucleic acid molecule as introduced into a host cell, thereby producing a transfected host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. The term vector is used interchangeably herein with "plasmid".

III. Overview of Several Embodiments

Provided herein are compositions for removing cyanuric acid and organic metabolites thereof from a liquid, which include at least one microbial cell culture, ground cells, extract thereof, or soluble protein fraction thereof, comprising cyanuric acid amidohydrolase, biuret cysteine hydrolase, and allophanate hydrolase, or a functional variants of at least one of the aforementioned hydrolases.

In particular embodiments, the composition is composed of the extract of a single microbial cell culture. In other embodiments, the composition includes a plurality of cultures or extracts from a plurality of cell cultures, and wherein the cyanuric acid amidohydrolase and allophanate hydrolase are in a separate culture or extract from the biuret cysteine hydrolase.

In other particular embodiments, the cyanuric acid amidohydrolase, allophanate hydrolase, and biuret cysteine hydrolase are expressed by at least one recombinant nucleic acid in the cell culture, such as a recombinant nucleic acid expressing one or more of the polypeptides described herein (e.g. polypeptide set forth as SEQ ID NOs 1-4 and 6). In one example, the cyanuric acid amidohydrolase and allophanate hydrolase are expressed genomically in the cell culture, and wherein the biuret cysteine hydrolase is expressed from a recombinant nucleic acid in the cell culture. In another example, the cyanuric acid amidohydrolase and allophanate hydrolase are expressed from at least one recombinant nucleic acid in the cell culture, and wherein the biuret cysteine hydrolase is expressed genomically in the cell culture.

In another embodiment of the described compositions, the cyanuric acid amidohydrolase, allophanate hydrolase, and biuret cysteine hydrolase are expressed genomically in the cell culture.

In a particular embodiment, the cyanuric acid amidohydrolase and allophanate hydrolase are from *Pseudomonas* spp., and wherein the biuret cysteine hydrolase is from *Rhizobium* spp.

Also described herein are compositions for removing cyanuric acid and organic metabolites thereof from a liquid, which include isolated cyanuric acid amidohydrolase, or a functional variant thereof, isolated allophanate hydrolase, or a functional variant thereof, and isolated biuret cysteine hydrolase, or a functional variant thereof. In particular embodiments of the composition, the isolated cyanuric acid amidohydrolase, isolated biuret amidohydrolase, and isolated allophanate hydrolase are from any microbe capable of producing the enzymes, and in more particular embodiments from *Pseudomonas* spp. Similarly, the isolated biuret cysteine hydrolase is from any microbe capable of producing the enzyme, such as *Rhizobium* spp. In other embodiments, the isolated cyanuric acid amidohydrolase is from *Pseudomonas* spp., the isolated biuret cysteine hydrolase is from *Rhizobium* spp., and the isolated allophanate hydrolase is from an additional microbial species, for example *Oleomonas sagaranensis*.

In some embodiments of the compositions described herein, the composition is in solution or is a dry powder. In other embodiments, the composition is formulated as a water-soluble tablet or a water-soluble container, or is bound to a solid substrate.

Further described herein are methods of removing cyanuric acid and organic metabolites thereof from a liquid including providing an effective amount of the described compositions to the liquid, thereby removing cyanuric acid and organic metabolites thereof from the liquid. Any liquid can be subject to the described methods, including water in a swimming pool, fountain, or decorative waterfall.

In particular embodiments, the described methods further comprise contacting the liquid with an ammonia-removal agent, such as on a column or an agent comprising zeolite, or in the form of an ammonia-removing enzyme prior to, concurrent with, or following the composition.

IV. Enzymatic Removal of Cyanuric Acid

Removal of cyanuric acid (CYA) from a body of water can be accomplished enzymatically. In one non-limiting example, the CYA degradation pathway of *Pseudomonas* sp. ADP, utilizes three hydrolases of the amidohydrolase family: cyanuric acid amidohydrolase (AtzD), biuret amidohydrolase (AtzE), and allophanate hydrolase (AtzF) to convert CYA into carbon dioxide and ammonia (described for example in (Shapir et al., *Appl. Environ. Microb.*, 72:2491-2495, 2006). According to this metabolic pathway, when fully metabolized 1 mole of CYA will yield 3 moles of ammonia.

Figure 2:
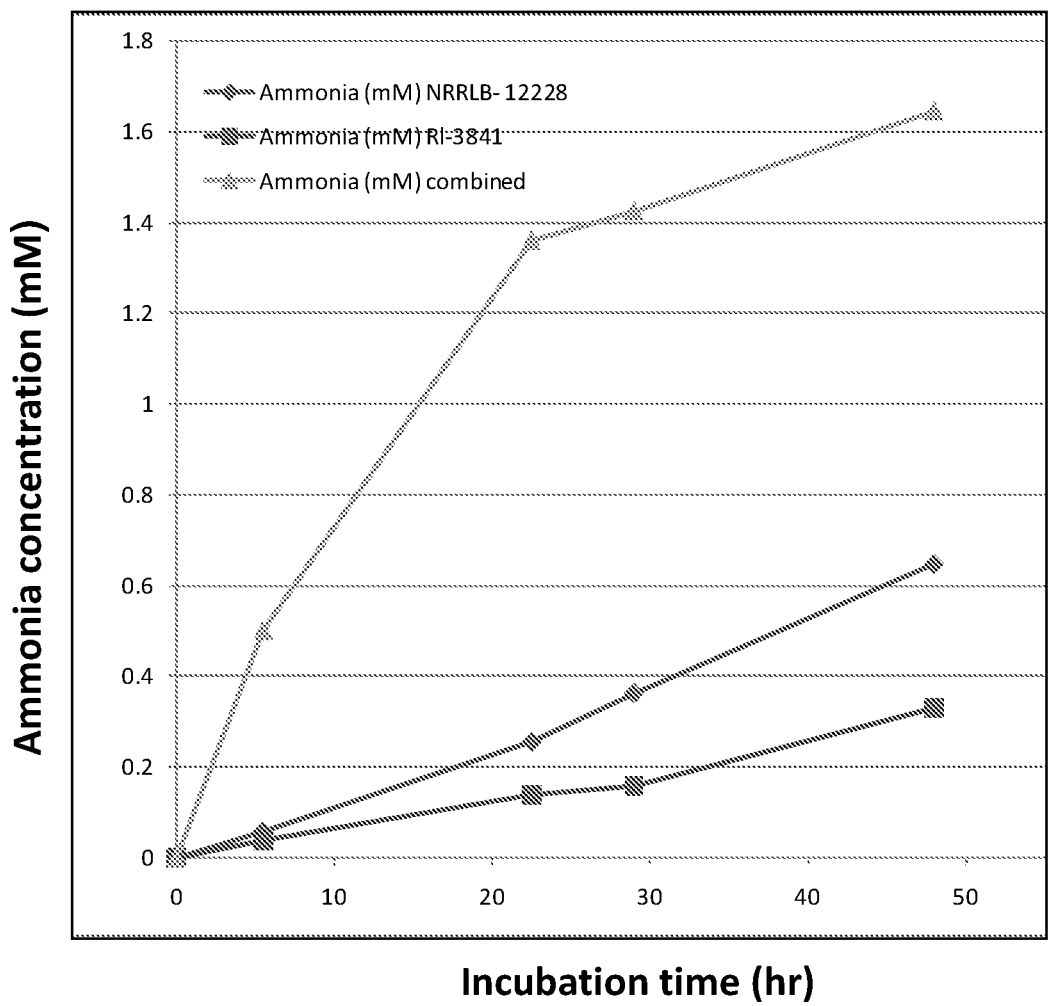
FIG. 2 is a graph showing Ammonia liberation following incubation of 0.5 mM CYA and endogenous enzymes. Crude extracts (diluted 1:200) of *Pseudomonas* NRRLB 12228 cells (diamonds), *Rhizobium leguminosarum* bv. *viciae* strain 3841 (squares), or a combination of the two (triangles), were incubated with 0.5 mM CYA in 10 mM sodium phosphate buffer for the indicated time points at 30° C. Ammonia concentrations were measured with Nessler Reagent kit.

As described in Example 1 and shown in FIGS. 1 and 2, a *Pseudomonas* NRRLB 12228 extract containing the three native amidohydrolase enzymes AtzD, AtzE, AtzF, respectively) can remove CYA from water. However, it was observed that the metabolic pathway does not proceed completely, and the expected 3 moles of ammonia are not produced per mole of CYA, an indication that CYA and its metabolites are not fully broken down by the *Pseudomonas* NRRLB 12228 extract, and remain in the water at potentially undesirable concentrations. This result indicates that compositions based solely on amidohydrolases, such as the *Pseudomonas* amidohydrolases or homologs thereof) will be ineffective at removing CYA and its metabolites from an environment. This observation is in part related to the ex vivo instability of biuret amidohydrolase (see Cameron et al, ACS Catal. 2011).

It has now been unexpectedly observed that the breakdown of CYA and its metabolites can be dramatically improved by a novel combination of a cell extract containing at least cyanuric acid amidohydrolase and allophanate hydrolase with an extract containing biuret cysteine hydrolase (a biuret hydrolase of the cysteine hydrolase superfamily) from *Rhizobium leguminosarum* bv. *viciae* strain 3841. Thus, the non-natural combination of enzymes from the amidohydrolase family and the cysteine hydrolase super-family can remove CYA and its metabolites more effectively than previously possible.

In view of this observation, described herein are compositions that can remove CYA and its metabolites from an environment, such as a body of water. The compositions contain at least three enzymatic components: cyanuric acid amidohydrolase and allophanate hydrolase; and one enzyme from the cysteine hydrolase super family: biuret cysteine hydrolase. In particular embodiments of the described compositions, biuret amidohydrolase is also included.

The cyanuric acid amidohydrolase of strain NRRLB-12227 of *Pseudomonas* spp. (Fruchey et al., *Appl Environ Microbiol*, 69: 3653-3657, 2003; Karns, *Appl Environ Microbiol*, 65:3512-3517, 1999) has been well characterized: it hydrolyses cyanuric acid to biuret and $CO_2$ with a $K_M$ of 0.05 mM, $V_{max}$ of 109 µmoles/min/mg at a turnover rate of 250 reactions per second and has an optimal catalytic pH of 8 at a temperature of 45° C. (see on-line at brendaenzymes.info/). The above $K_M$ value of 0.05 mM guarantees that at excess cyanuric acid concentrations such as 100 ppm, the enzyme will work at its maximal velocity. Using these enzymatic parameters of the cyanuric acid amidohydrolase isolated from *Pseudomonas* sp. strain NRRLB-12227 (Fruchey et al., *Appl Environ Microbiol*, 69: 3653-3657, 2003; Karns, *Appl Environ Microbiol*, 65:3512-3517, 1999), one can calculate that for a volume of 50 cubic meters containing 100 ppm of cyanuric acid, approximately 2.4 grams of cyanuric acid amidohydrolase and 16 hours are needed for a reduction of cyanuric acid from 100 ppm to 50 ppm in a 50 cube (50,000 L) swimming pool.

It will be appreciated that enzyme specific activity varies from enzyme to enzyme, and the above calculation is only illustrative. Similarly, the effective amount of each enzyme needed in each given application, for example, to reduce cyanuric acid from 100 ppm to 50 ppm will vary from enzyme to enzyme and will also depend on the amount of CYA desired to eliminate. It is understood that once the specific activity of any given enzyme is known, the effective amount can be determined. Moreover, it is understood that the overall speed of the breakdown of CYA and its metabolites can be increased by increased amounts of the described compositions or increased amounts of the constituent enzymes therein.

The *Pseudomonas* sp. ADP cyanuric acid amidohydrolase, biuret amidohydrolase (optionally), and allophanate hydrolase for use in the described compositions and methods have been described and sequenced. The respective amino acid sequence of each of these enzymes is shown in FIGS. 5A-C. It will be appreciated that functionally equivalent variants of these enzymes are within the scope of this disclosure and can be used in the compositions and methods as described.

In particular embodiments, each of the described cyanuric acid amidohydrolase, biuret amidohydrolase, or allophanate hydrolase enzymes have an amino acid sequence that is at least 60%, at least 70%, at least 80%, at least 85%, at least 90%, or at least 95, 96, 97, 98, or 99% identical to the amino acid sequence of cyanuric acid amidohydrolase, biuret amidohydrolase, or allophanate hydrolase, respectively, of a bacterium selected from the group consisting of *Acidovorax citrulli*, *Acidovorax citrulli* 12227, *Agrobacterium radiobacter*, *Cupriavidus basilensis*, *Gordonia rubripertincta*, *Hormodendrum* spp., *Klebsiella pneumonia*, *Moorella thermoacetica*, *Penicillium* spp., *Pseudomonas* spp., *Ralstonia pickettii*, and *Sporothrix schenckii*. These enzyme variants have equal or substantially similar activity to the wild type enzymes of the above mentioned bacteria, and in particular to that of the amino acid residue sequence of these enzymes of *Pseudomonas* strain NRRLB 12228 and *Oleomonas sagaranensis*, as set forth herein, and are described herein as "functional variants" of the described enzymes.

Similarly a biuret cysteine hydrolase enzyme for use in the described compositions is also described herein as a "functional variant" of the wild type enzyme, and which has an amino acid sequence that is at least 60%, at least 70%, at least 80%, at least 85%, at least 90%, or at least 95, 96, 97, 98, or 99% identical to the amino acid sequence of the biuret cysteine hydrolase of *Rhizobium leguminosarum* bv. *viciae* strain 3841 (shown herein as FIG. 6A; with the nucleic acid sequence shown as FIG. 6B).

Functional variants of the described enzymes also include recombinant modifications of wild type versions of the enzymes, such as modifications of one or more of the polypeptides set forth as SEQ ID NOs 1-4 and 6.

The cyanuric acid amidohydrolase, biuret amidohydrolase and allophanate hydrolase can all be provided in the described compositions in the form of whole cells, as whole cell powder, as ground whole cells, as components of whole cell extracts and/or can be purified from bacteria that naturally produce the enzymes, including recombinant variants thereof. Particular non-limiting examples of such bacteria include *Acidovoraxcitrulli*, *Acidovoraxcitrulli* 12227, *Agrobacterium radiobacter*, *Cupriavidus basilensis*, *Gordoniaru bripertincta*, *Hormodendrum* sp., *Klebsiella pneumonia*, *Moorella thermoacetica*, *Penicillium* spp., *Pseudomonas* spp., *Ralstonia Pickettii*, and *Sporothrix schenckii*.

Similarly, biuret cysteine hydrolase, a member of the cysteine hydrolase super enzyme family, can be provided in a whole cell extract, as whole cell powder, ground whole cells, or isolated from a naturally-producing source, including *Rhizobium* spp.

In particular embodiments, the cyanuric acid amidohydrolase, allophanate hydrolase, biuret cysteine hydrolase, and optionally, biuret amidohydrolase, are components of one or a plurality of combined microbial cell culture extracts, such as from one or more of the bacterial species listed above. In particular embodiments, the one or more cell culture extracts are whole cell culture extracts produced by standard methods or as whole cell powder. In other embodiments, the compositions are composed of whole cells expressing the necessary enzymes, which have been processed for introduction to an environment, such as a body of water. A non-limiting examples of such processing include dried cells (by freeze-drying or other method), which have been ground to a powder or powder like material.

In a particular embodiment, the cyanuric acid amidohydrolase, allophanate hydrolase, and optional biuret cysteine hydrolase enzymes are provided by a single cell culture or culture extract. In another embodiment, these enzymes are provided by multiple cell cultures or cell culture extracts. In those embodiments wherein multiple cultures or extracts provide the enzymes, each enzyme can be provided by a different species of bacteria in particular embodiments. For example, the cyanuric acid amidohydrolase can be provided by any species of microbe which encodes the enzyme or is capable of expressing it. Non-limiting examples of such microbes include *Acidovorax citrulli*, *Cupriavidus basilensis*, *Gordonia rubripertincta*, *Gordonia rubripertincta* 11, *Hormodendrum* sp., *Klebsiella pneumoniae*, *Moorella thermoacetica*, *Penicillium* spp., *Pseudomonas* spp., and *Sporothrix schenckii*, whereas the allophanate hydrolase can be provided by a different species of bacteria, such as *Oleomonas sagaranensis* (the amino acid sequence of which is shown in FIG. 7).

In a particular embodiment, the composition includes cyanuric acid amidohydrolase from *Pseudomonas* spp., biuret cysteine hydrolase from *Rhizobium* spp., and allophanate hydrolase from *Oleomonas sagaranensis*. The enzymes can be provided as part of whole cells, as ground whole cell powder or as whole cell extracts, soluble protein fractions thereof, or isolated soluble proteins.

In other embodiments the one or more cell culture extracts are a soluble protein-containing fraction of a cell extract. In such soluble fractions, the proteins are not purified from the extract soluble milieu, but they been isolated from much of the non-protein cellular material found in the whole cell extracts. A protein fraction may be obtained by methods well known in the art. For example, it may be obtained by adding to the soluble crude extract a kosmotropic salt, a non-ionic hydrophilic polymer, a polyelectrolyte or a polyvalent metallic ion.

In certain embodiments, the anion of said kosmotropic salt is selected from the group consisting of $PO_4^{3-}$, $SO_4^{2-}$, $COO^-$ and $Cl^-$ and the cation of said kosmotropic salt is selected from the group consisting of $NH_4^+$, $K^+$ and $Na^+$; the non-ionic hydrophilic polymer is selected from the group consisting of dextran and polyethylene glycol; the polyelectrolyte is selected from the group consisting of alginate, carboxymethycellulose, polyacrylic acid, tannic acid and polyphosphates; and the polyvalent metallic ion is selected from the group consisting of $Ca^{2+}$, $Mg^{2+}$, $Mn^{2+}$ and $Fe^2$. In other particular embodiments, the kosmotropic salt is ammonium sulfate.

In view of the current capabilities of the art, it will be appreciated that the encoding sequence for each of the enzymatic components of the described composition can be located genomically or as part of a recombinant expression plasmid.

In particular examples, a genomically-located coding sequence is a native part of the genome of the species of bacteria in the cultures used as described herein. In other embodiments, the coding sequence has been inserted into the bacterial genome, either in a non-native location in the native bacteria or in a non-native species. Multiple methods are known in the art for inserting a DNA sequence into a bacterial genome. Non-limiting examples include homologous recombination mediated genomic editing (e.g. CRISPR-mediated) and bacteriophage-mediated transduction.

In other embodiments, one or more enzymatic components of the described composition are encoded by a DNA sequence located on a recombinant expression plasmid that has been introduced (transformed) into a bacterium. Any bacteria capable of transformation and production of the described enzymes can be used to produce the described composition. Non-limiting examples of bacteria that may be transformed with an expression plasmid described herein include *Escherichia coli*, *Pseudomonas* spp., (for example strains NRRLB 12228 and ADP, and *Enterobacter cloacae* strain 99).

DNA expression plasmids are standard in the art, and it will be appreciated that any standard expression plasmid can be used to express one or more of the described enzymes. Such plasmids will minimally contain an origin of replication, selection sequence (such as, but not limited to an antibiotic resistance gene), and expression control sequences for the gene or genes of interest. Particular non-limiting examples of bacterial expression plasmids include IPTG-inducible plasmids, arabinose-inducible plasmids and the like. Other non-limiting examples of expression induction include light induction, temperature induction, and autoinduction DNA expression plasmids, and custom-made expression plasmids are commercially available from suppliers such as New England Biolabs (Ipswich, Mass.) and DNA 2.0 (Menlo Park, Calif.).

In particular embodiments, all of the enzymatic components of the described composition are genomically-encoded (i.e. encoded by and expressed from DNA sequence located in native or non-native genomic locations). In other embodiments, all of the enzymatic components are located on extra-genomic expression plasmids. In some embodiments, one or more of the enzymatic components is expressed from a plasmid, while the remaining enzymatic component(s) are genomically-encoded. In other embodiments, one or more of the enzymatic components is expressed genomically while the remaining enzymatic component(s) is expressed from a plasmid. For example, in one embodiment, the cell culture extracts contain cyanuric acid amidohydrolase, allophanate amidohydrolase, and biuret cysteine hydrolase that are genomically-encoded. In other examples the cyanuric acid amidohydrolase, allophanate hydrolase, and biuret cysteine hydrolase are all plasmid-encoded. In further examples, the cyanuric acid amidohydrolase and allophanate hydrolase are genomically-encoded, and the biuret cysteine hydrolase is plasmid encoded.

In particular embodiments, the described composition includes at least one isolated and purified enzymatic component. Therefore, in particular embodiments, all of the active enzymatic components of the composition have been isolated and purified. In other particular embodiments, at least one enzyme is provided by a cell culture extract, or soluble protein fraction thereof, while the remaining enzymatic components are isolated and purified.

Methods of protein purification are standard in the art (for example, see McGettrick and Worrall, *Methods in Molec. Biol.* 244:29-35, 2004). As described above, the amidohydrolases and cysteine hydrolase for use in the described composition can be expressed genomically or from a recombinant plasmid. Regardless of source, the described enzymes can be isolated and purified as known in the art, using any system able to isolate the expressed enzymes. In a particular example, the expressed enzymes contain a polyhistadine (e.g., HisX6) tag for use in standard $Ni^{2+}$ affinity chromatography. In another example, the expressed enzymes have an N-terminal or C-terminal glutathione-S-transferase (GST) tag for isolation with glutathione and Strep tag which allows the purification and detection of proteins by affinity chromatography, size exclusion chromatography, immunoprecipitation, and other similar protein purification methods known in the art.

The described compositions, whether containing cell culture extracts/fractions or isolated and purified components, can be formulated in any form for use as an additive in environmental purification system, such as water disinfection.

In particular embodiments, the composition (containing the enzymes) is formulated as a liquid or liquid-like suspension, slurry, or gel, all of which can be provided in a water-soluble tablet or pellet, similar to pharmaceutical liquigel formulations. In certain embodiments, the enzymes of the described compositions are soluble. In other embodiments, one or more of the described enzymes are immobilized onto a solid substrate, which is then applied to the liquid to be cleansed of CYA. In still other embodiments, the composition is formulated as a dry powder in which the enzymes have been lyophilized, which can be further processed into a dissolvable tablet. Additives that can be optionally added to such liquid and dry formulations are standard in the art and include potassium phosphate, phosphate buffered saline solution, or dextran.

In other particular embodiments, liquid/semi-liquid, and dry formulations can be further provided in a water-soluble sack, envelope, sachet, and the like. Such water-soluble materials are standard and are commercially available from suppliers including Solupak (Manchester, England) Applied Business Techniques Ltd (Worcester. England), and Harmless Packing for our Future (Ipswich, UK).

In a further embodiment, the described compositions can be provided in a kit that contains the described compositions and instructions for its use in removing CYA and its metabolites from an environment, such as a swimming pool or water reservoir. Additional components of such kits can include chlorine reducing-providing agents, CYA-measuring agents, a thiosulfate supplying agent, such as sodium thiosulfate, and ammonia clean-up materials.

V. Methods of Removing Cyanuric Acid and its Metabolites from an Environment

Additionally described herein are methods for removing CYA and its metabolites from an environment. Undesirably high concentrations of CYA and its metabolites can be a particular problem in swimming pools and other bodies of water, such as reservoirs that are disinfected by chlorinating agent. At elevated levels, for example 100 ppm, CYA forms a "chlorine lock" which significantly reduces the disinfecting efficacy off the chlorinating agent. The methods described herein reduce CYA levels, but also break down CYA's metabolites biuret and allophanate more significantly than previous methods. Previous methods reduced CYA levels with combinations of amidohydrolase enzymes: *Pseudomanas* cyanuric acid amidohydrolase, biuret amidohydrolase, and allophanate hydrolase. As described herein however (see Example 1), such combinations failed to produce the 3 moles of ammonia expected from metabolic break-down of 1 mole of CYA therefore did not reach reaction completion. The current methods, utilizing a non-natural combination of enzymes from two enzyme families, significantly reach reaction completion as seen by the amount of ammonia released, and therefore provides compositions and methods that have not yet been described and are significant improvements on previous methods.

The described methods include providing to an environment, such as a body of water, an effective amount of the described compositions such that the CYA and its metabolites are removed, producing ammonia and carbon dioxide. It will be appreciated that an "effective amount" of the described enzymes can be determined in relation to the specific activity of the given enzyme and the amount of substrate needed to undergo degradation within the swimming pool water.

In particular embodiments, the body of water is a swimming pool, decorative fountain or bathing fountain.

In still further embodiments the body of water is an ornamental water source including garden or other ornamental fountains and waterfalls.

In the described methods, the CYA-removal composition can be provided in solid or liquid formulations, as indicated above. Such formulations can be added as bulk powders/liquids, pre-measured tablets or gelatin-coated liquigels, or in water-soluble containers such as sachets, envelopes, or sacks.

In particular embodiments, the described methods are a part of a system of water disinfection and purification that includes aspects of chlorinating the water, CYA measurement, CYA removal once the levels rise above 50 ppm, and ammonia removal. It will be appreciated that such systems can include, inter alia, filters, pumps, heaters, and delivery methods of each of the system components.

The hazard of an ammonia solution has been characterized from "irritant", through "corrosive" to "dangerous to the environment" depending on its concentration. Generally, this is due to formation of ammonium ion from ammonia, which in turn bonds with free chlorine anions to produce chloramine skin and eye irritants. Thus, the described methods may include addition of an $NH_4^+$ binding agent or an agent that detoxifies or degrades $NH_4^+$. In certain embodiments, the ammonia (or ammonium) binding agent is selected from a zeolite such as clinoptilolite $(Na,K,Ca)^{2-} 3Al_3(Al,Si)_2Si_{13}O_{36} \cdot 12H_2O)$ or phillipsite, peat (an accumulation of partially decayed vegetation), Vermiculite and Enso® bark, made of pine bark, and said agent that detoxifies $NH_4^+$ is selected from magnesium hydrogen phosphate and the like, which converts ammonia to sodium hydroxymethane sulfonate, or an agent which converts ammonia to aminomethane sulfonate. Other ammonia/ammonium binding or degradation materials that can be used to remove ammonia/ammonium resultant from CYA breakdown include sodium nitrite-containing compounds, plants, such as duckweed, and nitrogen fixation enzymes. In particular embodiments, ammonia can be enzymatically converted to nitrogen by the activity or ammonia monooxygenase, hydrazine hydrolase, and hydrazine dehydrogenase. In particular embodiments, the $NH_4^+$ binding agent that is added is clinoptilolite.

In certain embodiments, the $NH_4^+$ binding agent or agents that detoxifies or degrades $NH_4^+$ is housed in a container selected from a column, housing or casing, such as a filter or netting, wherein water comprising $NH_3$ or $NH_4^+$ can flow through the container and contact the binding agent or agent that detoxifies $NH_3$, or it is bound to particles that are added to water comprising $NH_3$ or $NH_4^+$. In particular embodiments, the $NH_3$ or $NH_4^+$-bound container can be removed from the body of water and the $NH_3$ or $NH_4^+$ can be removed from the container, such as by treatment with sodium chloride.

The following examples are provided to illustrate certain particular features and/or embodiments. These examples should not be construed to limit the disclosure to the particular features or embodiments described.

EXAMPLES

Example 1: CYA Metabolism with Cell Culture Extract Combinations

This example shows that a combination of whole cell extracts from *Pseudomonas* NRRLB 12228 and *Rhizobium leguminosarum* bv. *viciae* strain 3841 provides synergistic removal of CYA and complete removal of its metabolites in comparison to either extract alone.

CYA (starting concentration of 0.5 mM) degradation was measured in 10 mM sodium phosphate buffer. To separate CYA samples was added whole cell extracts of *Pseudomonas* NRRLB 12228 and *Rhizobium leguminosarum* bv. *viciae* strain 3841, alone and in combination both bacterial strains were grown on minimal medium supplemented with CYA and glucose as a sole source for nitrogen and carbon respectively. At the end of logarithmic phase cells were collected by centrifugation washed X2 with 10 mM sodium phosphate buffer pH 8.0 and resuspended in the same buffer containing proteases inhibitor. Cell walls were disrupted by Sonicator 4 cycles 1 min each. Cell lysate was centrifuge for 30 min. and supernatant containing the enzymes was collected.

CYA concentration was measured over time following addition of cell extracts, and using the C401 kit according to manufacturer's instructions.

As shown in FIG. 1, the *Rhizobium leguminosarum* bv. *viciae* strain 3841 extract alone did not significantly remove CYA from the solution. In contrast, CYA concentrations was significantly reduced by either the *Pseudomonas* NRRLB 12228 extract alone or with *Rhizobium leguminosarum* bv. *viciae* strain 3841. Notably, the combination extract worked faster than the *Pseudomonas* alone (compare results at the 10 minute time point). However both extracts reduced CYA below detectable amounts by 20 minutes.

CYA removal is only the first step in CYA metabolism. The complete breakdown of biuret and then allophanate can be indicated by ammonia release. Therefore, to determine "reaction completion," ammonia release was detected over several hour incubation of 0.5 mM CYA in 10 mM sodium phosphate buffer with the same extracts described above. Ammonia concentrations were measured with Nessler Reagent kit.

FIG. 2 shows that at nearly the end of 48 hour incubation, extract from *Rhizobium leguminosarum* bv. *viciae* strain 3841 resulted in release of about 0.3 mM ammonia; while extract from *Pseudomonas* NRRLB 12228 resulted in release of about 0.7 mM ammonia. In contrast, the combined extracts resulted in release of close to 1.5 mM of ammonia. This indicates a synergistic interaction between the two extracts, and likely between the cyanuric acid amidohydrolase, allophanate hydrolase (both from *Pseudomonas*) and the biuret cysteine hydrolase (from *Rhizobium*).

Figure 3:
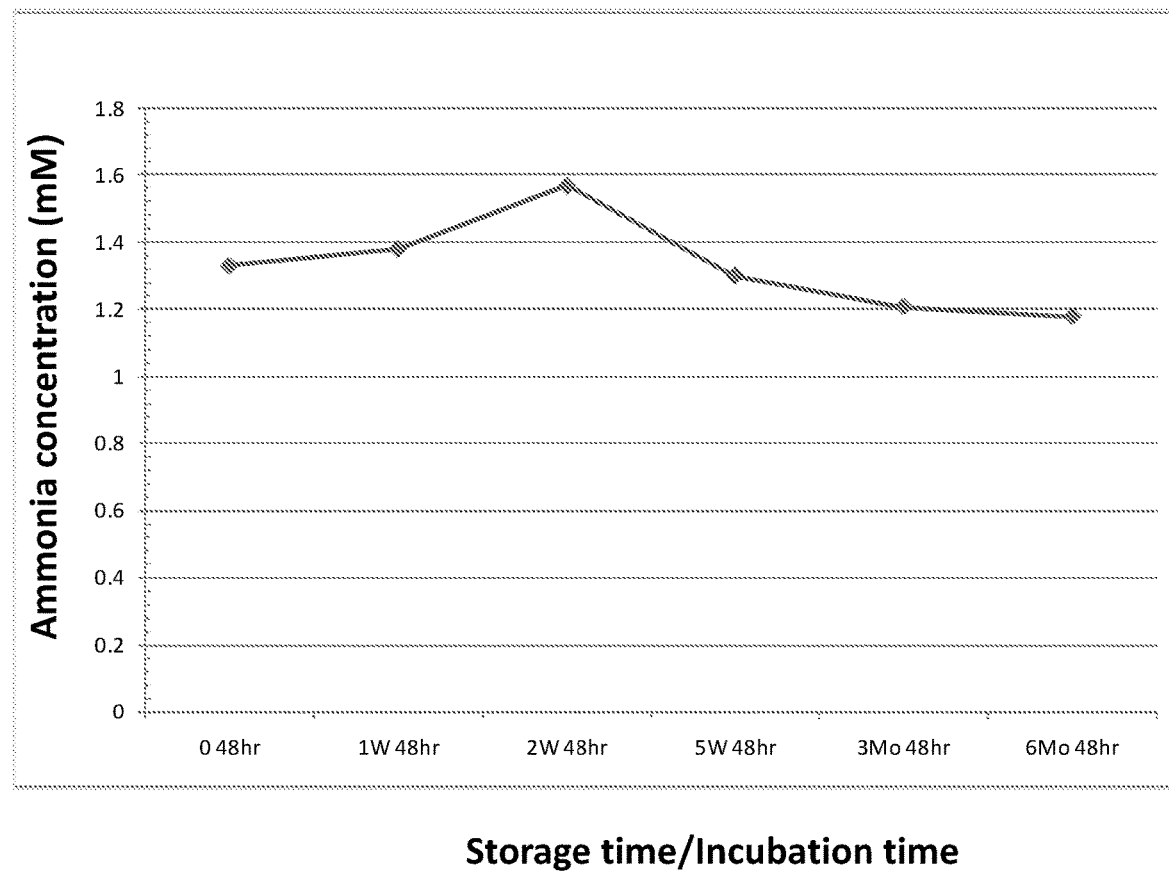
FIG. 3 is a graph showing ammonia liberation following incubation of 0.5 mM CYA with endogenous enzymes after storage at −20° for the indicated times. Combined extracts of *Pseudomonas* NRRLB 12228 and *Rhizobium leguminosarum* bv. *viciae* strain 3841 were incubated with 0.5 mM CYA in 10 mM sodium phosphate buffer for 48 hours at 30° C. Ammonia concentrations were measured with Nessler Reagent kit.

The stability of the synergistic enzymatic activities was next tested. The combined extract described above was stored at −20° for six months. Periodically, aliquots of the combined extract were removed and incubated with 0.5 mM CYA in 10 mM sodium phosphate buffer for 48 hours at 30° C. Ammonia concentrations were measured with Nessler Reagent kit. As shown in FIG. 3, the ability for the combined extracts to break down CYA and its metabolites remained largely stable; even after six months.

Lastly, the breakdown of CYA and resultant ammonia release were determined in swimming pool water using the combined bacterial extracts. The results are shown in FIG. 4.

Example 2: Expression of Recombinant CYA Metabolic Enzymes

This example shows the expression and positive identification of recombinant enzymes for use in the claimed compositions and methods.

Recombinant nucleic acid plasmids expressing Cyanuric acid amidohydrolase, Biuret Cysteine hydrolase, and Allophanate hydrolase from *Pseudomonas* NRRLB 12228 and *Oleomonas sagaranensis*, were constructed into pET41b (The pET-41 series is designed for cloning and high-level expression of peptide sequences fused with the 220 aa GST.Tag™ protein.) according to standard methods (by GenScript Services, Piscataway, N.J.) Each of the four plasmids were then transformed into *E. coli* BL21 bacteria. Positive transformants were grown at 37° C. overnight in 5 ml LB media supplemented with 50 µg/ml Kanamycin. The following day, 0.5 ml of the starter was added to 50 ml LB media (1:100) and grown at the same conditions to OD600~0.50. IPTG was added to final concentration of 1 mM and each induced culture was grown at the temperatures and for the times indicated on FIG. 8. Cultures were harvested by centrifugation. 1 ml from each harvested culture was sonicated and 150 µl was set aside (total proteins), the samples were centrifuged and 150 µl of the supernatant were taken (sup proteins). The 150 µl of each sample was resuspended in sample buffer (SAB) and used for Coomassie gel analysis and Western Blot according to standard protocols.

Figure 8:
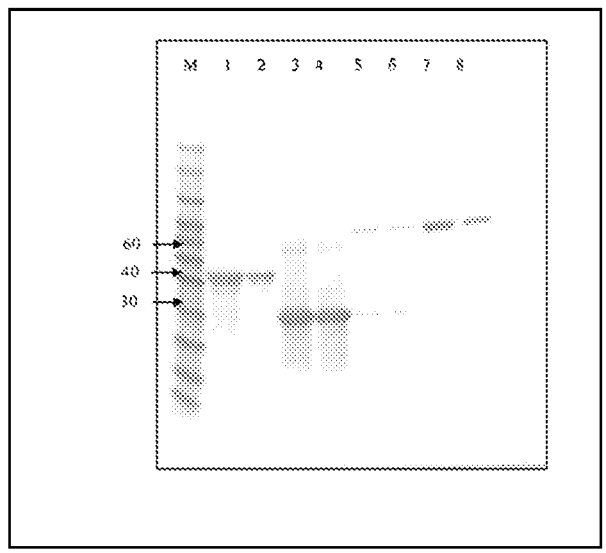
FIG. 8 shows a Western blot analysis of expressed recombinant cyanuric acid amidohydrolase, cysteine hydrolase and Allophanate hydrolase from *Pseudomonas* and from *Oleomonas sagaranensi* proteins. The bottom panel shows corresponding lane identity, along with induction time and temperature.

Western blot was performed on the highest expressed sample of each protein as determined from the Coomasie gels. Primary antibody: Anti His Tag Antibody, mAb, Mouse (GenScript, Piscataway, N.J., Cat #:A00186S, lot 11 G000326 (10 µg). This lyophilized antibody was resuspended in 40 µl water (0.254 µl) and stored at −20° C. until used. Secondary antibody: Alkaline Phosphatase, conjugated Affini Pure Goat Anti-Mouse IgG (Jackson ImmunoResearch Laboratories, Inc., West Grove, Pa.; Cat:115-055-003. lot 122966). The lyophilized conjugate was resuspended in 1 ml water (to 0.6 mg/ml), then 1 ml of 100% glycerol was added, kept at −20° C. until used. Representative results of the Western blot are shown in FIG. 8, and demonstrate specific induction of desired hydrolase enzymes, which can then be used in the described methods of CYA removal from an environment, such as a swimming pool.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method of removing cyanuric acid and organic metabolites thereof from a liquid, comprising:
providing to the liquid an effective amount of a composition comprising at least one microbial cell culture extract, or soluble protein fraction thereof, comprising cyanuric acid amidohydrolase, biuret cysteine hydrolase, and allophanate hydrolase, or functional variants thereof, thereby removing cyanuric acid and organic metabolites thereof from the liquid,
wherein the cyanuric acid amidohydrolase and allophanate hydrolase are from *Pseudomonas* spp., and wherein the biuret cysteine hydrolase is from *Rhizobium* spp., and wherein the organic metabolites are biuret and allophanate.

2. The method of claim 1, wherein the liquid is water in a swimming pool, fountain, decorative waterfall or any other water reservoir.

3. The method of claim 1, further comprising contacting the liquid with an ammonia-removal agent prior to, concurrent with, or following the composition.

4. The method of claim 3, wherein the ammonia removal agent is part of a column or is an ammonia-removing enzyme.

5. The method of claim 1, wherein the composition comprises the extract of a single microbial cell culture.

6. The method of claim 1, wherein the composition comprises a plurality of extracts from a plurality of cell cultures, and wherein the cyanuric acid amidohydrolase and allophanate hydrolase are in a separate extract from the biuret cysteine hydrolase.

7. The method of claim 1, wherein at least one of the cyanuric acid amidohydrolase, allophanate hydrolase, and biuret cysteine hydrolase are expressed by at least one recombinant nucleic acid in the cell culture.

8. The method of claim 1, wherein the cyanuric acid amidohydrolase and allophanate hydrolase are expressed genomically in the cell culture, and wherein the biuret cysteine hydrolase is expressed from a recombinant nucleic acid in the cell culture.

9. The method of claim 1, wherein the cyanuric acid amidohydrolase and allophanate hydrolase are expressed from at least one recombinant nucleic acid in the cell culture, and wherein the biuret cysteine hydrolase is expressed genomically in the cell culture.

10. The method of claim 1, wherein the cyanuric acid amidohydrolase, allophanate hydrolase, and biuret cysteine hydrolase are expressed genomically in the cell culture.

11. The method of claim 1, wherein the composition is in solution or is a dry powder.

12. The method of claim 1, wherein the composition is formulated as a water-soluble tablet or a water-soluble container.

\* \* \* \* \*

SEQUENCE LISTING

<160> NUMBER OF SEQ ID NOS: 6

<210> SEQ ID NO 1
<211> LENGTH: 363
<212> TYPE: PRT
<213> ORGANISM: Pseudomonas aeruginosa

<400> SEQUENCE: 1

Met Tyr His Ile Asp Val Phe Arg Ile Pro Cys His Ser Pro Gly Asp
1               5                   10                  15

Thr Ser Gly Leu Glu Asp Leu Ile Glu Thr Gly Arg Val Ala Pro Ala
            20                  25                  30

Asp Ile Val Ala Val Met Gly Lys Thr Glu Gly Asn Gly Cys Val Asn
        35                  40                  45

Asp Tyr Thr Arg Glu Tyr Ala Thr Ala Met Leu Ala Ala Cys Leu Gly
    50                  55                  60

Arg His Leu Gln Leu Pro Pro His Glu Val Glu Lys Arg Val Ala Phe
65                  70                  75                  80

Val Met Ser Gly Gly Thr Glu Gly Val Leu Ser Pro His His Thr Val
                85                  90                  95

Phe Ala Arg Arg Pro Ala Ile Asp Ala His Arg Pro Ala Gly Lys Arg
            100                 105                 110

Leu Thr Leu Gly Ile Ala Phe Thr Arg Asp Phe Leu Pro Glu Glu Ile
        115                 120                 125

Gly Arg His Ala Gln Ile Thr Glu Thr Ala Gly Ala Val Lys Arg Ala
    130                 135                 140

Met Arg Asp Ala Gly Ile Ala Ser Ile Asp Leu His Phe Val Gln
145                 150                 155                 160

Val Lys Cys Pro Leu Leu Thr Pro Ala Lys Ile Ala Ser Ala Arg Ser
                165                 170                 175

Arg Gly Cys Ala Pro Val Thr Thr Asp Thr Tyr Glu Ser Met Gly Tyr
            180                 185                 190

Ser Arg Gly Ala Ser Ala Leu Gly Ile Ala Leu Ala Thr Glu Glu Val
        195                 200                 205

Pro Ser Ser Met Leu Val Asp Glu Ser Val Leu Asn Asp Trp Ser Leu
    210                 215                 220

Ser Ser Ser Leu Ala Ser Ala Ser Ala Gly Ile Glu Leu Glu His Asn
225                 230                 235                 240

Val Val Ile Ala Ile Gly Met Ser Glu Gln Ala Thr Ser Glu Leu Val
                245                 250                 255

Ile Ala His Gly Val Met Ser Asp Ala Ile Asp Ala Ala Ser Val Arg
            260                 265                 270

Arg Thr Ile Glu Ser Leu Gly Ile Arg Ser Asp Asp Glu Met Asp Arg
        275                 280                 285

Ile Val Asn Val Phe Ala Lys Ala Glu Ala Ser Pro Asp Gly Val Val
    290                 295                 300

Arg Gly Met Arg His Thr Met Leu Ser Asp Ser Asp Ile Asn Ser Thr
305                 310                 315                 320

Arg His Ala Arg Ala Val Thr Gly Ala Ala Ile Ala Ser Val Val Gly
                325                 330                 335

His Gly Met Val Tyr Val Ser Gly Gly Ala Glu His Gln Gly Pro Ala
            340                 345                 350

Gly Gly Gly Pro Phe Ala Val Ile Ala Arg Ala
        355                 360

<210> SEQ ID NO 2
<211> LENGTH: 457
<212> TYPE: PRT
<213> ORGANISM: Pseudomonas aeruginosa

<400> SEQUENCE: 2

Met Lys Thr Val Glu Ile Ile Glu Gly Ile Ala Ser Gly Arg Thr Ser
1               5                   10                  15

Ala Arg Asp Val Cys Glu Glu Ala Leu Ala Thr Ile Gly Ala Thr Asp
            20                  25                  30

Gly Leu Ile Asn Ala Phe Thr Cys Arg Thr Val Glu Arg Ala Arg Ala
        35                  40                  45

Glu Ala Asp Ala Ile Asp Val Arg Arg Ala Arg Gly Glu Val Leu Pro
    50                  55                  60

Pro Leu Ala Gly Leu Pro Tyr Ala Val Lys Asn Leu Phe Asp Ile Glu
65                  70                  75                  80

Gly Val Thr Thr Leu Ala Gly Ser Lys Ile Asn Arg Thr Leu Pro Pro
                85                  90                  95

Ala Arg Ala Asp Ala Val Leu Val Gln Arg Leu Lys Ala Ala Gly Ala

```
            100                 105                 110
Val Leu Leu Gly Gly Leu Asn Met Asp Glu Phe Ala Tyr Gly Phe Thr
        115                 120                 125
Thr Glu Asn Thr His Tyr Gly Pro Thr Arg Asn Pro His Asp Thr Gly
        130                 135                 140
Arg Ile Ala Gly Gly Ser Ser Gly Gly Ser Gly Ala Ala Ile Ala Ala
145                 150                 155                 160
Gly Gln Val Pro Leu Ser Leu Gly Ser Asp Thr Asn Gly Ser Ile Arg
                165                 170                 175
Val Pro Ala Ser Leu Cys Gly Val Trp Gly Leu Lys Pro Thr Phe Gly
                180                 185                 190
Arg Leu Ser Arg Arg Gly Thr Tyr Pro Phe Val His Ser Ile Asp His
            195                 200                 205
Leu Gly Pro Leu Ala Asp Ser Val Glu Gly Leu Ala Leu Ala Tyr Asp
        210                 215                 220
Ala Met Gln Gly Pro Asp Pro Leu Asp Pro Gly Cys Ser Ala Ser Arg
225                 230                 235                 240
Ile Gln Pro Ser Val Pro Val Leu Ser Gln Gly Ile Ala Gly Leu Arg
                245                 250                 255
Ile Gly Val Leu Gly Gly Trp Phe Arg Asp Asn Ala Gly Pro Ala Ala
                260                 265                 270
Arg Ala Ala Val Asp Val Ala Ala Leu Thr Leu Gly Ala Ser Glu Val
            275                 280                 285
Val Met Trp Pro Asp Ala Glu Ile Gly Arg Ala Ala Ala Phe Val Ile
        290                 295                 300
Thr Ala Ser Glu Gly Gly Cys Leu His Leu Asp Asp Leu Arg Ile Arg
305                 310                 315                 320
Pro Gln Asp Phe Glu Pro Leu Ser Val Asp Arg Phe Ile Ser Gly Val
                325                 330                 335
Leu Gln Pro Val Ala Trp Tyr Leu Arg Ala Gln Arg Phe Arg Arg Val
                340                 345                 350
Tyr Arg Asp Lys Val Asn Ala Leu Phe Arg Asp Trp Asp Ile Leu Ile
            355                 360                 365
Ala Pro Ala Thr Pro Ile Ser Ala Pro Ala Ile Gly Thr Glu Trp Ile
        370                 375                 380
Glu Val Asn Gly Thr Arg His Pro Cys Arg Pro Ala Met Gly Leu Leu
385                 390                 395                 400
Thr Gln Pro Val Ser Phe Ala Gly Cys Pro Val Val Ala Ala Pro Thr
                405                 410                 415
Trp Pro Gly Glu Asn Asp Gly Met Pro Ile Gly Val Gln Leu Ile Ala
                420                 425                 430
Ala Pro Trp Asn Glu Ser Leu Cys Leu Arg Ala Gly Lys Val Leu Gln
            435                 440                 445
Asp Thr Gly Ile Ala Arg Leu Lys Cys
        450                 455

<210> SEQ ID NO 3
<211> LENGTH: 605
<212> TYPE: PRT
<213> ORGANISM: Pseudomonas aeruginosa

<400> SEQUENCE: 3

Met Asn Asp Arg Ala Pro His Pro Glu Arg Ser Gly Arg Val Thr Pro
1               5                   10                  15
```

-continued

Asp His Leu Thr Asp Leu Ala Ser Tyr Gln Ala Ala Tyr Ala Ala Gly
            20                  25                  30

Thr Asp Ala Ala Asp Val Ile Ser Asp Leu Tyr Ala Arg Ile Lys Glu
            35                  40                  45

Asp Gly Glu Asn Pro Ile Trp Ile Ser Leu Leu Pro Leu Glu Ser Ala
50                      55                  60

Leu Ala Met Leu Ala Asp Ala Gln Gln Arg Lys Asp Lys Gly Glu Ala
65                  70                  75                  80

Leu Pro Leu Phe Gly Ile Pro Phe Gly Val Lys Asp Asn Ile Asp Val
                85                  90                  95

Ala Gly Leu Pro Thr Thr Ala Gly Cys Thr Gly Phe Ala Arg Thr Pro
            100                 105                 110

Arg Gln His Ala Phe Val Val Gln Arg Leu Val Asp Ala Gly Ala Ile
            115                 120                 125

Pro Ile Gly Lys Thr Asn Leu Asp Gln Phe Ala Thr Gly Leu Asn Gly
            130                 135                 140

Thr Arg Thr Pro Phe Gly Ile Pro Arg Cys Val Phe Asn Glu Asn Tyr
145                 150                 155                 160

Val Ser Gly Gly Ser Ser Gly Ser Ala Val Ala Val Ala Asn Gly
                165                 170                 175

Thr Val Pro Phe Ser Leu Gly Thr Asp Thr Ala Gly Ser Gly Arg Ile
            180                 185                 190

Pro Ala Ala Phe Asn Asn Leu Val Gly Leu Lys Pro Thr Lys Gly Leu
            195                 200                 205

Phe Ser Gly Ser Gly Leu Val Pro Ala Ala Arg Ser Leu Asp Cys Ile
210                 215                 220

Ser Val Leu Ala His Thr Val Asp Asp Ala Leu Ala Val Ala Arg Val
225                 230                 235                 240

Ala Ala Gly Tyr Asp Ala Asp Ala Phe Ser Arg Lys Ala Gly Ala
                245                 250                 255

Ala Ala Leu Thr Glu Lys Ser Trp Pro Arg Arg Phe Asn Phe Gly Val
            260                 265                 270

Pro Ala Ala Glu His Arg Gln Phe Phe Gly Asp Ala Glu Ala Glu Ala
            275                 280                 285

Leu Phe Asn Lys Ala Val Arg Lys Leu Glu Glu Met Gly Gly Thr Cys
290                 295                 300

Ile Ser Phe Asp Tyr Thr Pro Phe Arg Gln Ala Ala Glu Leu Leu Tyr
305                 310                 315                 320

Ala Gly Pro Trp Val Ala Glu Arg Leu Ala Ala Ile Glu Ser Leu Ala
                325                 330                 335

Asp Glu His Pro Glu Val Leu His Pro Val Val Arg Asp Ile Ile Leu
            340                 345                 350

Ser Ala Lys Arg Met Ser Ala Val Asp Thr Phe Asn Gly Ile Tyr Arg
            355                 360                 365

Leu Ala Asp Leu Val Arg Ala Ala Glu Ser Thr Trp Glu Lys Ile Asp
            370                 375                 380

Val Met Leu Leu Pro Thr Ala Pro Thr Ile Tyr Thr Val Glu Asp Met
385                 390                 395                 400

Leu Ala Asp Pro Val Arg Leu Asn Ser Asn Leu Gly Phe Tyr Thr Asn
                405                 410                 415

Phe Val Asn Leu Met Asp Leu Ser Ala Ile Ala Val Pro Ala Gly Phe
            420                 425                 430

Arg Thr Asn Gly Leu Pro Phe Gly Val Thr Phe Ile Gly Arg Ala Phe

```
            435                 440                 445
Glu Asp Gly Ala Ile Ala Ser Leu Gly Lys Ala Phe Val Glu His Asp
450                 455                 460

Leu Ala Lys Gly Asn Ala Ala Thr Ala Ala Pro Pro Lys Asp Thr Val
465                 470                 475                 480

Ala Ile Ala Val Val Gly Ala His Leu Ser Asp Gln Pro Leu Asn His
                    485                 490                 495

Gln Leu Thr Glu Ser Gly Gly Lys Leu Arg Ala Thr Thr Arg Thr Ala
                500                 505                 510

Pro Gly Tyr Ala Leu Tyr Ala Leu Arg Asp Ala Thr Pro Ala Lys Pro
            515                 520                 525

Gly Met Leu Arg Asp Gln Asn Ala Val Gly Ser Ile Glu Val Glu Ile
        530                 535                 540

Trp Asp Leu Pro Val Ala Gly Phe Gly Ala Phe Val Ser Glu Ile Pro
545                 550                 555                 560

Ala Pro Leu Gly Ile Gly Thr Ile Thr Leu Glu Asp Gly Ser His Val
                    565                 570                 575

Lys Gly Phe Leu Cys Glu Pro His Ala Ile Glu Thr Ala Leu Asp Ile
                580                 585                 590

Thr His Tyr Gly Gly Trp Arg Ala Tyr Leu Ala Ala Gln
            595                 600                 605

<210> SEQ ID NO 4
<211> LENGTH: 233
<212> TYPE: PRT
<213> ORGANISM: Rhizobium leguminosarum

<400> SEQUENCE: 4

Met Asp Ala Met Val Glu Thr Asn Arg His Phe Ile Asp Ala Asp Pro
1               5                   10                  15

Tyr Pro Trp Pro Tyr Asn Gly Ala Leu Arg Pro Asp Asn Thr Ala Leu
                20                  25                  30

Ile Ile Ile Asp Met Gln Thr Asp Phe Cys Gly Lys Gly Gly Tyr Val
            35                  40                  45

Asp His Met Gly Tyr Asp Leu Ser Leu Val Gln Ala Pro Ile Glu Pro
        50                  55                  60

Ile Lys Arg Val Leu Ala Ala Met Arg Ala Lys Gly Tyr His Ile Ile
65                  70                  75                  80

His Thr Arg Glu Gly His Arg Pro Asp Leu Ala Asp Leu Pro Ala Asn
                85                  90                  95

Lys Arg Trp Arg Ser Gln Arg Ile Gly Ala Gly Ile Gly Asp Pro Gly
                100                 105                 110

Pro Cys Gly Arg Ile Leu Thr Arg Gly Glu Pro Gly Trp Asp Ile Ile
            115                 120                 125

Pro Glu Leu Tyr Pro Ile Glu Gly Glu Thr Ile Ile Asp Lys Pro Gly
        130                 135                 140

Lys Gly Ser Phe Cys Ala Thr Asp Leu Glu Leu Val Leu Asn Gln Lys
145                 150                 155                 160

Arg Ile Glu Asn Ile Ile Leu Thr Gly Ile Thr Thr Asp Val Cys Val
                165                 170                 175

Ser Thr Thr Met Arg Glu Ala Asn Asp Arg Gly Tyr Glu Cys Leu Leu
                180                 185                 190

Leu Glu Asp Cys Cys Gly Ala Thr Asp Tyr Gly Asn His Leu Ala Ala
            195                 200                 205
```

Ile Lys Met Val Lys Met Gln Gly Gly Val Phe Gly Ser Val Ser Asn
210                 215                 220

Ser Ala Ala Leu Val Glu Ala Leu Pro
225                 230

<210> SEQ ID NO 5
<211> LENGTH: 702
<212> TYPE: DNA
<213> ORGANISM: Rhizobium leguminosarum

<400> SEQUENCE: 5
atggacgcga tggtcgaaac caaccggcat tttatcgacg ccgatccgta tccgtggccc    60
tataacggag ctctgaggcc tgacaatacc gccctcatca tcatcgacat gcagacggat   120
ttctgcggca agggcggtta tgtcgaccac atgggctacg acctgtcgct ggtgcaggcg   180
ccgatcgaac ccatcaaacg cgtgcttgcc gccatgcggg ccaagggtta tcacatcatc   240
cacacccgcg agggccaccg ccccgacctc gccgatctgc cagcaaacaa acgctggcgc   300
tcgcaacgga tcggggccgg catcggtgat cccggcccct gcggccgaat cctgacgcgt   360
ggcgaacccg gctgggacat catccccgaa ctctacccga tcgaaggcga cgatcatc    420 gacaagcccg gcaagggttc gttctgcgcc accgacctcg aactcgtcct caaccagaaa   480
cgcatcgaga acattatcct caccgggatc accaccgatg tctgcgtctc gacgacgatg   540
cgcgaggcga acgaccgcgg ctacgaatgc ctgctgctgg aggactgctg tggtgcgacc   600
gactacggaa accacctcgc cgccatcaag atggtgaaga tgcagggcgg cgtcttcggc   660
tcggtctcca attccgcggc tctagtcgag gcgctgccct ga                      702

<210> SEQ ID NO 6
<211> LENGTH: 600
<212> TYPE: PRT
<213> ORGANISM: Oleomonas sagaranensis

<400> SEQUENCE: 6

Met Thr Leu Pro Lys Met Leu Thr Ile Gly Thr Leu Ala Ala Ala Tyr
1               5                   10                  15

Glu Ala Gly Thr Leu Thr Pro Leu Asp Val Ile Glu Gly Val Ile Glu
                20                  25                  30

Arg Leu Asn Ala Trp Pro Asp Pro Ala Val Trp Ile Ser Arg Phe Ser
            35                  40                  45

Asp Asp Asp Leu Arg Ala Ala Ala Lys Ala Leu Val Asp Ala Gly Gly
        50                  55                  60

Pro Ser Pro Asp Lys Pro Leu Trp Gly Ile Pro Phe Ala Val Lys Asp
65                  70                  75                  80

Asn Ile Asp Cys Ala Gly Leu Asp Thr Thr Ala Ala Cys Pro Ala Phe
                85                  90                  95

Ala Tyr Thr Pro Thr Gln Asp Ala Thr Val Val Ala Arg Leu Arg Ala
                100                 105                 110

Ala Gly Ala Ile Pro Val Gly Lys Thr Asn Leu Asp Gln Phe Ala Thr
            115                 120                 125

Gly Leu Asn Gly Thr Arg Ser Pro Tyr Gly Ala Pro Arg Ser Val Phe
        130                 135                 140

Asn Ala Asp Tyr Ile Ser Gly Gly Ser Ser Gly Ser Ala Val Ser
145                 150                 155                 160

Val Gly Ala Gly Ile Val Ala Phe Ser Leu Gly Thr Asp Thr Ala Gly
                165                 170                 175

-continued

```
Ser Gly Arg Val Pro Ala Ser Phe Asn Asn Leu Val Gly Val Lys Pro
            180                 185                 190

Ser Lys Gly Met Phe Ser Asn Thr Gly Leu Val Pro Ala Cys Arg Ser
        195                 200                 205

Leu Asp Cys Ile Ser Ile Phe Ala Ala Thr Ala Gly Glu Ala Asp Phe
    210                 215                 220

Val Arg Arg Ile Ala Ala Ala Leu Asp Pro Ser Asp Pro Phe Ser Arg
225                 230                 235                 240

Asp Leu Pro Asp Val Val Leu Pro Thr Glu Gly Leu Arg Val Gly Val
                245                 250                 255

Pro Val Gly Ala Glu Arg Glu Phe Phe Gly Asp Ser Ala Asn Glu Ala
            260                 265                 270

Ile Tyr Val Gly Ala Ile Glu Thr Met Lys Ala Leu Gly Cys Ser Ile
        275                 280                 285

Val Glu Ile Asp Phe Ala Pro Phe Arg Glu Ala Ala Asn Leu Leu Tyr
    290                 295                 300

Ser Gly Pro Trp Val Ala Glu Arg Leu Ala Ala Val Glu Ala Phe His
305                 310                 315                 320

Ala Ala His Ala Asp Ala Met Asp Pro Asn Val Arg Thr Ile Val Glu
                325                 330                 335

Gly Ala Phe Gly Val Thr Ala Val Asp Ala Phe Arg Gly Ile Tyr Ala
            340                 345                 350

Leu Glu Gly Tyr Arg Gln Lys Thr Ala Ser Thr Trp Ala Met Val Asp
        355                 360                 365

Ile Leu Leu Leu Pro Thr Thr Pro Leu Phe Pro Lys Val Ser Glu Met
    370                 375                 380

Leu Ala Asp Pro Ile Gly Leu Asn Ser Lys Leu Gly Arg Tyr Thr Asn
385                 390                 395                 400

Phe Val Asn Leu Met Asp Cys Ala Gly Ile Ala Val Pro Ala Gly Phe
                405                 410                 415

Arg Pro Asp Gly Leu Pro Phe Gly Val Thr Leu Ile Gly Pro Ala Phe
            420                 425                 430

Ser Asp Ala Ala Leu Ala Val Trp Gly Asp Arg Leu His Lys Ala Ser
        435                 440                 445

Ala Thr Gly Phe Gly Leu Asp Thr Thr Ala Asp Leu Ala Ala Met Pro
    450                 455                 460

Ala Pro Glu Gly Pro Asp Val Glu Arg Ile Glu Val Val Val Val Gly
465                 470                 475                 480

Ala His Leu Ser Gly Met Pro Leu Asn Pro Gln Leu Thr Ser Gly Gly
                485                 490                 495

Gly Val Leu Val Lys Ser Cys Arg Thr Ala Pro Asp Tyr Arg Leu Tyr
            500                 505                 510

Ala Leu Pro Gly Thr Val Pro Pro Lys Pro Gly Leu Ile His Ser Pro
        515                 520                 525

Gly Phe Asp Gly Pro Gly Leu Ala Val Glu Val Trp Ala Leu Pro Pro
    530                 535                 540

Ala Ala Phe Gly Arg Phe Val Ala Ala Ile Pro Ala Pro Leu Gly Ile
545                 550                 555                 560

Gly Lys Val Thr Leu Asp Asp Gly Ser Asp Val Ser Gly Phe Leu Cys
                565                 570                 575
```

```
Glu Ala His Ala Leu Glu Gly Ala Val Glu Ile Thr Ala Leu Gly Gly
            580                 585                 590

Trp Arg Ala Tyr Cys Ala Ala Lys
        595                 600
```